(12) United States Patent
Dimitrov (10) Patent No.: US 10,761,166 B2
(45) Date of Patent: Sep. 1, 2020

(54) IMAGING SYSTEM FOR SINGLE VOXEL SPECTROSCOPY

(71) Applicant: KONINKLIJKE PHILIPS N.V., Eindhoven (NL)

(72) Inventor: Ivan Dimitrov, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 656 days.

(21) Appl. No.: 15/512,998

(22) PCT Filed: Sep. 11, 2015

(86) PCT No.: PCT/IB2015/056957
§ 371 (c)(1),
(2) Date: Mar. 21, 2017

(87) PCT Pub. No.: WO2016/046686
PCT Pub. Date: Mar. 31, 2016

(65) Prior Publication Data
US 2017/0299677 A1 Oct. 19, 2017

Related U.S. Application Data

(60) Provisional application No. 62/055,983, filed on Sep. 26, 2014.

(51) Int. Cl.
*G01R 33/465* (2006.01)
*G01R 33/483* (2006.01)
(Continued)

(52) U.S. Cl.
CPC ............ *G01R 33/465* (2013.01); *A61B 5/055* (2013.01); *G01R 33/485* (2013.01);
(Continued)

(58) Field of Classification Search
CPC ................................. G01R 33/483; G01R 33/465; G01R 33/5608; G01R 33/4833; G01R 33/485; G01R 33/56; A61B 5/055
See application file for complete search history.

(56) References Cited

U.S. PATENT DOCUMENTS 4,899,109 A 2/1990 Tropp et al.
6,529,002 B1 3/2003 Kim et al.
(Continued)

FOREIGN PATENT DOCUMENTS

JP 2001187038 A 7/2001

OTHER PUBLICATIONS

Neustadter D.et al.:"Interactive Inhomogeneity Map for use in Single Magnetic Resonance Spectroscopy Localization",Proceedings of the International Society for Magnetic Resonance in Medicine, 21st Annual Meeting & Exhibition,Apr. 20, 2013 (Apr. 20, 2013), p. 2571.

(Continued)

*Primary Examiner* — Jermele M Hollington
*Assistant Examiner* — Suresh K Rajaputra (57) ABSTRACT

A guide map is created for use in placing a spectroscopic single voxel in a region of interest in single voxel magnetic resonance spectroscopy. An anatomical planning image of the region of interest is obtained through MRI. As a spectroscopy voxel is stepped across the region of interest, characteristics of the magnetic field used in the MRI are measured at each location of the imaging voxel, and a guide-FWHM map indicative of the homogeneity/inhomogeneity of the magnetic field over the region of interest is derived using the measurements. The guide map is created by overlaying the guide-FWHM map on the anatomical planning image. A spectroscopic single voxel of a size corresponding to that of the spectroscopy voxel is placed (Continued)

within the region of interest as per the guide map. Then spectral data is acquired from the region of interest confined to the single voxel.

23 Claims, 5 Drawing Sheets

(51) Int. Cl.
  *G01R 33/485* (2006.01)
  *G01R 33/56* (2006.01)
  *A61B 5/055* (2006.01)
  *G01R 33/565* (2006.01)
  *G01R 33/24* (2006.01)

(52) U.S. Cl.
  CPC ..... *G01R 33/4833* (2013.01); *G01R 33/5608* (2013.01); *G01R 33/243* (2013.01); *G01R 33/56563* (2013.01)

(56) References Cited

U.S. PATENT DOCUMENTS

| | | | |
|---|---|---|---|
| 7,348,775 B2 | 3/2008 | Weiger et al. | |
| 7,689,262 B2 | 3/2010 | Kruger et al. | |
| 2010/0085050 A1* | 4/2010 | Dong | G01R 33/243 324/309 |
| 2015/0077107 A1 | 3/2015 | Sharp et al. | |

OTHER PUBLICATIONS

Solanky B S et al: "In vivo magnetic Resonance spectroscopy detection of combined glutamate-glutamine in healthy upper cervical cord at 3 T",NMR in Biomedicine John Wiley & Sons Ltd. UK, vol. 26, No. 3, Mar. 201 (Mar. 2013), pp. 357-366.
Drost Dick J et al: "Proton magnetic resonance spectroscopy in the brain: Report of AAPM MR Task Group #9", Medical Physics, AIP, Melville, NY, US, vol. 29, No. 9,Sep. 1, 2002 (Sep. 1, 2002), pp. 2177-2197.

* cited by examiner

IMAGING SYSTEM FOR SINGLE VOXEL SPECTROSCOPY

CROSS REFERENCE TO RELATED APPLICATIONS

This application is a U.S. national phase application of International Application No. PCT/IB2015/056957, filed on Sep. 11, 2015, which claims the benefit of U.S. provisional Application Ser. No. 62/055,983 filed on Sep. 26, 2014 and is incorporated herein by reference.

BACKGROUND

Magnetic resonance imaging (MRI) allows images of tissue to be captured in vivo and in a non-invasive manner. MRI is unlike X-rays or CT scans in that MRI employs magnetic fields to produce an image, as opposed to ionizing radiation. Therefore, MRI is relatively harmless. Accordingly, MRI is now used in a range of applications in the field of medical diagnostics. In clinical MRI, a patient is placed within a scanner of an MRI system and a region of interest of the patient is exposed to a magnetic field generated by a scanner of the MRI system also referred to as a localizer. Basically, the frequency of the magnetic field is selected to resonate (i.e., excite) certain atoms making up the tissue in the region of interest, and emissions of the excited atoms are captured and analyzed to produce an image of the tissue.

Magnetic resonance spectroscopy (MRS), also known as nuclear magnetic resonance (NMR) spectroscopy, combines magnetic resonance imaging and spectroscopic techniques. Basically, in MRS, an MRI system is controlled to first perform an MRI scan that captures an image of an anatomical region of interest in a sample or patient, and the image is used to plan for the spectroscopy including for helping to identify a localized volume within the region of interest where the spectroscopy is to be carried out. One aspect of controlling the MRI system to perform the spectroscopy is to "shim" the magnetic field generated by the MRI system in an attempt to maximize the homogeneity of the field over the localized volume within the region of interest. A spectra or spectrum of emissions from the tissue confined to this localized volume within the shimmed magnetic field are captured and analyzed.

The spectrum/spectra acquired by MRS contains information about metabolites making up the tissue in the localized volume within the region of interest. Therefore, MRS is a technique of choice to acquire images and information of tumors, especially tumors such as those which may be present in the brain. Such information can be used to diagnose and stage the tumors.

Furthermore, MRS may be classified as single voxel MRS or multi-voxel MRS (also referred to as chemical shift imaging).

In single voxel MRS, as the name implies, an anatomical planning image of the region of interest is obtained through conventional MRI, and a single volume (the single voxel) is defined and located in the region of interest under the control of technician based on an observation of the anatomical planning image and his or her experience with the protocol of the suspected pathology. At this time, as described above, the magnetic field is shimmed for the single voxel. As a result, a spectrum of magnetic resonances from the single volume is obtained. Metabolite concentrations can be measured from the spectrum to yield information on characteristics of the tissue within the region of the single voxel.

In CSI, spectra of emissions are obtained from several volumes in a 2D slice of interest or a 3D region of interest. Thus, although CSI is advantageous over single voxel MRS in that a larger sample in a region of interest can be examined, it is disadvantageous in that it provides a lower signal-to-noise ratio (SNR) and requires a longer scan time.

However, the clinical success of using single voxel MRS depends strongly on not only the shimming of the magnetic field but the location where the single voxel is placed within the region of interest.

Specifically, placing the single voxel in an area of high magnetic field homogeneity can result in good single voxel results, while placing the single voxel in an area of poor field homogeneity, i.e., in an area of magnetic field inhomogeneity, can lead to a low signal-to-noise ratio (SNR). The process of single voxel placement can be operator dependent, leading to poor results especially when conducted by an untrained or relatively inexperienced MRI technician.

SUMMARY

According to a representative embodiment, there is provided a method for use in magnetic resonance imaging, which comprises exposing a region of interest to a magnetic field, producing an anatomical planning image of the region of interest from signals emitted from the region of interest as a result of its exposure to the magnetic field, analyzing the magnetic field for its homogeneity over the region of interest, and based on the analysis of the magnetic field, producing a map of areas of the anatomical planning image of different degrees of homogeneity of the magnetic field.

The magnetic field may be produced using a localizer of a magnetic resonance imaging (MRI) system.

Single voxel magnetic resonance spectroscopy (MRS) may be conducted by placing a spectroscopic single voxel within the anatomical region of interest as guided by the map.

Single voxel magnetic resonance spectroscopy (MRS) may be conducted by placing a spectroscopic single voxel within the anatomical region of interest as guided by the map produced by a method in which the localizer produces the magnetic field, but also by operating the MRI system to acquire a spectrum of magnetic resonances from that part of the anatomical region of interest confined to the spectroscopic single voxel.

In this case, the anatomical planning image and the spectrum of magnetic resonances may be obtained sequentially while a patient, undergoing the MRS, remains within the MRI system.

Alternatively, the anatomical planning image may be obtained as a separate scan of a patient before the patient enters the MRI system for a scan that produces the spectrum of magnetic resonances.

The analyzing of the magnetic field may include stepping a spectroscopic voxel across the region of interest, measuring a characteristic of the magnetic field at the spectroscopic voxel each time the spectroscopic voxel is located at a new position as the result of the stepping, and calculating FWHM in the characteristic of the magnetic field at each position of the spectroscopic voxel.

The guide map may be produced by demarcating at least three areas of the anatomical planning image in which the degrees of homogeneity of the magnetic field are different from one another.

The guide map may be produced by displaying contours of the at least three areas of the anatomical planning image in which the degrees of homogeneity of the magnetic field are different from one another.

The guide map may also be produced by color coding these at least three areas.

In addition, the size of the spectroscopic single voxel may be calculated based on the guide map.

For instance, the size of the single voxel may be calculated based on the size of a region of overlap between the area of the guide map where the homogeneity of the magnetic field is the greatest and a demarcated region of the anatomical planning image.

According to another representative embodiment, there is provided a method single voxel magnetic resonance spectroscopy (MRS) method, which includes generating an anatomical planning image from a region of interest using a magnetic field, producing and displaying a map of areas of the anatomical planning image having different degrees of homogeneity of the magnetic field, and subsequently generating a spectrum of resonances emitted from a single voxel located in that part of the region of interest confined to the single spectroscopic voxel.

According to this representative embodiment, the map may be produced by stepping a spectroscopic voxel across the region of interest, measuring a characteristic of the magnetic field at the spectroscopic voxel each time the imaging spectroscopic voxel is located at a new position as the result of the stepping, and calculating FWHM in the characteristic of the magnetic field at each position of the spectroscopic voxel.

The map may be produced by demarcating at least three areas of the anatomical planning image in which the degrees of homogeneity of the magnetic field are different from one another.

In addition a size of the spectroscopic single voxel may be calculated based on the map.

For instance, the size of the spectroscopic single voxel may be calculated based on the size of a region of overlap between the area of the map where the homogeneity of the magnetic field is the greatest and a demarcated region of the anatomical planning image.

According to still another representative embodiment, there is provided a method of conducting single voxel magnetic resonance spectroscopy (MRS), which includes obtaining an anatomical planning image of a region of interest using a magnetic field, positioning a single spectroscopic voxel within the region of interest, and acquiring a spectrum of magnetic resonances emitted from that part of the region of interest confined to the single spectroscopic voxel, and in which the single spectroscopic voxel is positioned within the region of interest by observing a display of a map of areas of the anatomical planning image having different degrees of homogeneity of the magnetic field, and operating a magnetic resonant imaging (MRI) system, as guided by the display, to place the single spectroscopic voxel at a location in the region of interest.

According to this representative embodiment, the anatomical planning image and the acquiring of the spectrum of magnetic resonances may be effected sequentially while a patient, undergoing the MRS, remains within the MRI system.

Alternatively, the anatomical planning image may be obtained as a separate scan of a patient before the patient enters the MRI system for a scan that produces the spectrum of magnetic resonances.

According to still another representative embodiment, there is provided an imaging system that includes a magnet/coil device operable to expose a region to a magnetic field, and a control system that includes a control unit that controls the operation of the magnet/coil device and receives signals emitted from the region as a result of its exposure to the magnetic field, and a processor operable to produce a spectroscopic single voxel, and in which the control system is configured with overlay data representative of areas of an anatomical planning image of different degrees of homogeneity of a magnetic field used to create the anatomical planning image, and in which the processor and the control unit are operatively connected such that the magnetic resonance imaging system is operable in a single voxel spectroscopy mode in which the single voxel is locatable within a region of interest of the anatomical planning image on the basis of the overlay data, the magnetic/coil device is controlled by the control unit to expose a region confined to the spectroscopic single voxel to a magnetic field, and the control unit acquires a spectrum of magnetic resonances emitted from that region confined to the spectroscopic single voxel.

According to this representative embodiment, the system may also include a console including a display, and the control system may be operable to generate a map of the areas of the anatomical planning image of different degrees of homogeneity of the magnetic field, and may be operatively connected to the console such that the map can be displayed on the display during the single voxel spectroscopy mode.

The map may include at least three areas of the anatomical planning image in which the degrees of homogeneity of the magnetic field are different from one another.

The map may have contour lines at boundaries between adjacent ones of the at least three areas.

In this case, the at least three areas may be color coded to differentiate themselves from one another.

The processor may also be configured to calculate a size of the spectroscopic single voxel based on the overlay data.

In this case, the size of the single voxel may be calculated based on the size of a region of overlap between an area where the homogeneity of the magnetic field is the greatest and a demarcated region of the anatomical planning image.

Also, the control system may be configured to process the anatomical planning image and thereby demarcate a region of interest in the anatomical planning image, calculate the size of the spectroscopic single voxel, and locate the spectroscopic single voxel within the region of interest based on the overlay data, all automatically while the system is in the single voxel spectroscopy mode.

According to still another representative embodiment, there is provided a computer readable non-transistory medium storing a program, executable by a controller, for controlling an imaging system. The computer readable medium comprises: an anatomical planning image code segment for producing an anatomical planning image of the region of interest from signals emitted from the region of interest as a result of its exposure to the magnetic field; an analyzing code segment for analyzing the magnetic field for its homogeneity over the region of interest, based on the analyzing of the magnetic field; and a map producing code segment for producing a map of areas of the anatomical planning image of different degrees of homogeneity of the magnetic field, based on the analyzing of the magnetic field.

According to a representative embodiment, the computer readable medium further comprises a first pre-scan code segment for controlling the imaging system to acquire the anatomical planning image using a magnetic field, and a second pre-scan code segment for controlling the imaging system to acquire magnetic field data of the magnetic field used to produce the anatomical planning image and to produce overlay data from the anatomical planning image and the magnetic field data.

According to a representative embodiment, the map producing code segment further comprises a map generating code segment for generating a map of the overlay data and for controlling the imaging system to display the map.

According to a representative embodiment, the first pre-scan code segment comprises a code segment for an image processor to process the anatomical planning image to produce segmentation data representative of demarcations of the region of interest, the second pre-scan code segment comprise a code segment for producing the overlay data on the basis of the segmentation data, and computer readable medium further comprises a single voxel operating code segment for calculating a size of a spectroscopic single voxel on the basis of the overlay data.

According to a representative embodiment, the single voxel spectroscopy operating code segment comprises a locating code segment for locating the spectroscopic single voxel within the region of interest on the basis of the overlay data.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials and methods that are within the purview of one of ordinary skill in the art may be used in accordance with the representative embodiments.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

Relative terms, such as "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be below that element. Where a first device is said to be connected or coupled to a second device, this encompasses examples where one or more intermediate devices may be employed to connect the two devices to each other.

As used in the specification and appended claims, the terms 'a', 'an' and 'the' include both singular and plural referents, unless the context clearly dictates otherwise. Thus, for example, 'a device' includes one device and plural devices.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

As used in the specification and the appended claims and in addition to its ordinary meaning, the term 'approximately' means to within an acceptable limit or amount to one having ordinary skill in the art. For example, 'approximately the same' means that one of ordinary skill in the art would consider the items being compared to be the same.

Furthermore, the term "patient" as used in this specification is not restricted to human beings and encompasses any subject susceptible to MRI techniques, i.e., encompasses anatomical matter in a broad sense. The term "scan" may refer to a scan consisting of a single image frame acquisition pass as well as scanning techniques in which a series of individual acquisition passes—which are equal in terms of MR parameters and contrasts—are made, i.e., a scan including a plurality of separate image frames. The term "size" will be clear in context, e.g., will generally refer to the volume of a cube in the case in which the size of a 3D feature is being referred to. Other terminology used herein for the purpose of describing particular examples or representative embodiments is to be given the plain meaning as understood in the art and is otherwise to be taken in context.

Also, the terms "comprises" or "comprising" when used in this specification specifies the presence of stated features or processes but does not preclude the presence or additional features or processes.

The present teachings relate generally to the imaging of samples, including the tissue of patients, using magnetic fields. In particular, the teachings relate to magnetic resonance spectroscopy (MRS). Beneficially, the single voxel MRS method of an embodiment provides improved imaging. Moreover, a method of an embodiment reduces the dependence of the quality of the results of an MRS scan on the skill level of the technician performing the scan. In addition, a method of an embodiment provides a display, which an MRI technician can use to optimize the placement of a single voxel when conducting single voxel MRS.

Before a description of the techniques and methods of representative embodiments proceeds, an MRI system 1 that may be used to carry out the present teachings will be described with reference to FIG. 1.

The exemplary MRI system 1 comprises an MRI examination chamber or magnet room 3, inside which a patient 2 is positioned for examination. The MRI system 1 also comprises a magnet/coil device 4 disposed within the examination chamber 3 so as to extend around the patient 2 within the examination chamber 3. The magnet/coil device 4 includes various functional units (not shown) adapted for subjecting the patient 2 to a specific magic field used to elicit nuclear magnetic resonance signals from a particular location 2a (e.g., from the brain denoted by "X") inside the patient 2 and, in particular, from a region of interest (ROI) at that particular location (e.g., from a region within the brain).

The MRI system 1 also includes a control system 5 connected to the examination chamber 3 by a transceiver link 6. On a basic level the control system 5 comprises a control unit 7 for controlling operations of the units constituting the magnet/coil device 4, and for receiving the patient's NMR data, such as MRI data and data for spectroscopic analysis. Generally, the control unit 7 can be implemented in numerous ways (e.g., such as with dedicated hardware) to perform various functions discussed herein. A "processor" is one example of a controller, which employs one or more microprocessors that may be programmed using software (e.g., microcode) to perform various functions discussed herein. The control unit 7 may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, microcontrollers, application specific integrated circuits (ASICs), and field-programmable gate arrays (FPGAs).

In various implementations, the control unit 7 may be associated with one or more storage media (generically referred to herein as "memory," e.g., volatile and non-volatile computer memory such as random-access memory (RAM), read-only memory (ROM), programmable read-only memory (PROM), electrically programmable read-only memory (EPROM), electrically erasable and programmable read only memory (EEPROM), universal serial bus (USB) drive, floppy disks, compact disks, optical disks, magnetic tape, etc.). In some implementations, the storage media may be encoded with one or more programs that, when executed on the control unit 7, perform at least some of the functions discussed herein. Various storage media may be fixed within the control unit 7 or may be transportable, such that the one or more programs stored thereon can be loaded into a processor or controller so as to implement various aspects of the present teachings discussed herein. The terms "program," "computer program," or "instructions" are used herein in a generic sense to refer to any type of computer code or code segment (e.g., software or microcode) that can be employed to program the control unit 7.

Furthermore, the control system 5 comprises a data processing unit 8 for processing the data and a registration unit 9 for image registration, both of which are connected with the control unit 7. The control system 5 also comprises a prospective motion correcting unit 10 (PMC unit) and a geometry unit 11, the latter for defining, storing, and updating predefined scan geometries. Both the PMC unit 10 and the geometry unit 11 are connected with the control unit 7, too. The control system 5 is further connected with a user console 12 by which the MRI system 1 can be operated by a technician.

On a lower hierarchical level, the control unit 7 comprises a control processor 7.1, a transceiver 7.2, a pulse generator 7.3, a memory 7.4, and a (gradient) amplifier 7.5 by which the control unit 7 controls the operation of the examination chamber 3, e.g., by transmitting RF pulses to the RF coils of the magnet/coil device 4 for generating a specific magnetic field inside the patient 2, and by receiving from the magnet/coil device 4 the NMR signals emitted from the ROI 2b. Generally, the operation of the control unit 7 is controlled by the processor 7.1 in connection with control programs (not shown) stored in the memory 7.4, e.g., for modification of the RF pulses and gradient waveforms generated by the pulse generator 7.3 in operative connection with the gradient amplifier 7.5.

The data processing unit 8 of the control system 5 comprises an image processor 8.1, an image buffer 8.2, and an archive 8.3. By means of these elements the data processing unit 8 can temporarily store NMR image data received by the control unit 7, for performing standard image processing procedures, e.g. Fourier transformation, thus deriving a particular desired image data format, and for storing the latter quasi permanently for archiving purposes.

The registration unit 9 of the control system 5 comprises a registration processor 9.1 and a memory 9.2, which are conjunctively operative to register scans relative to each other, i.e., to compare different scan images and to derive from the comparison information as to a deviation between the scan images.

The PMC unit 10 of the control system 5 may also be adapted for prospective motion control with respect to a modification of scan parameters during a time-sliced acquisition of image data, i.e., within a time series constituting a single scan. To this end the MRI system 1 may further comprise external position determining means 14 operatively connected to both the examination chamber 3 and the control system 5, e.g., a camera for measuring a position of the patient 2. Otherwise, PMC can be performed using orbital MR navigator signals or fiducial markers.

The geometry unit 11 is operative to predefine scan geometries which may be shared under a plurality of different scanning scenarios in terms of MR parameters and contrasts, as generated by the control unit 7, and to provide these geometries to the control unit 7 to accordingly elicit NMR signals from the patient 2. To this end, the geometry unit 11 of the control system 5 comprises a geometry processor 11.1, a memory 11.2 configured with or for storing code related to scan geometry, geometry generating means 11.3, geometry transformation generating means 11.4, and geometry updating means 11.5.

The user console 12 of the MRI system 1 comprises a processor 12.1, and input means 12.2 and output means 12.2 controlled by the processor 12.1. The input means 12.2 allows the MRI technician to control the operation of the MRI system 1 and may comprise a keyboard/mouse. The output means 12.3 may display menus and the like for use in selecting the programs that control the operation of the MRI system 1, as well as data and images generated by the MRI system 1, and may comprise a display screen. The menus may be pop up menus of various patient protocols, scan modes, operating parameters, etc. Thus, the MRI technician can control and influence the operation of the MRI system 1 using the input and output means 12.1 and 12.2.

The MRI system 1 is only an example of an MRI system that may be adapted for use in carrying out the present teachings. That is, it will be clear to those skilled in the art that MRI systems having functional units, e.g. units 7-11, arranged and configured differently than those shown in and described with reference to FIG. 1 may be used instead.

Next, a method of conducting single voxel magnetic resonance spectroscopy (MRS) will be described with reference to FIGS. 1, 2A and 2B. The method includes an MRI process (S100) for obtaining an anatomical planning image of a region of interest (ROI), and a spectroscopic process (S200) for obtaining spectral data from a single voxel located within the ROI. The anatomical planning image and the spectrum of magnetic resonances may be obtained sequentially while a patient, undergoing the MRS, remains within the MRI system. Alternatively, the anatomical planning image may be obtained as a separate scan of a patient before the patient enters the MRI system for a scan that produces the spectral data.

Figure 1:
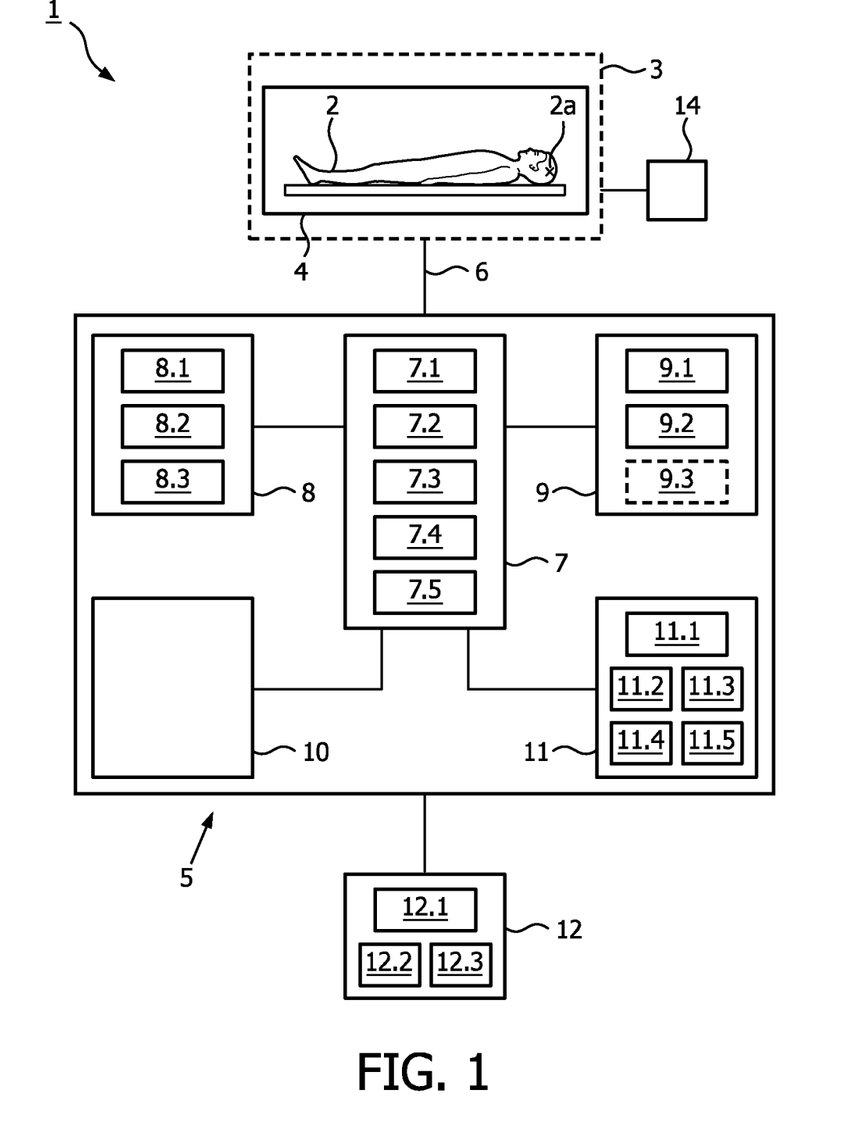
FIG. 1 is a block diagram of an example of an MRI system according to a representative embodiment.
Figure 2A:
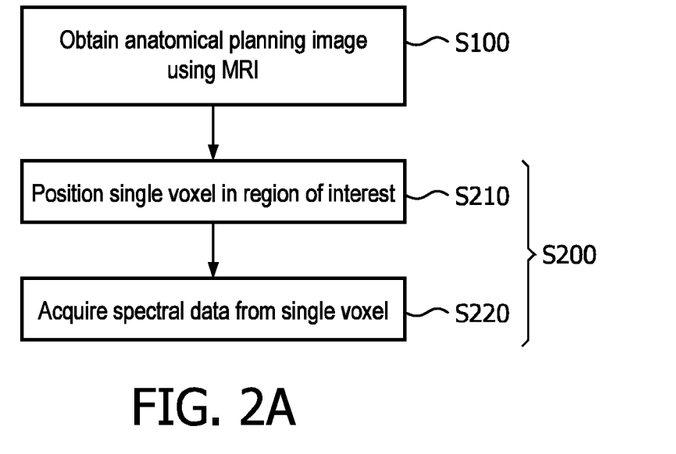
FIG. 2A is a flowchart of an MRS method according to a representative embodiment.
Figure 2B:
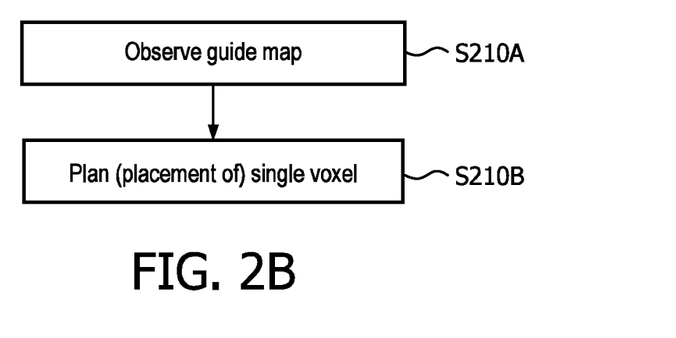
FIG. 2B is a flowchart of a process used to position the single voxel in the MRS method shown in FIG. 2A, according to according to a representative embodiment.

The anatomical planning image of the region of interest (ROI) may be obtained by an MRI technician by placing a patient in an examination chamber 3 of the MRI system 1 of FIG. 1, and selecting the protocol for an MRI scan of the ROI.

For example, in the case in which the single voxel MRS is used to acquire information from an ROI in the brain, the first steps performed by an MRI technician may be to assemble a brain coil as part of the magnet/coil device 4 of the MRI system, and to help load the patient into the examination chamber such that the patient's head becomes positioned in the brain coil. Next, the MRI technician may call up a "Patient Information" menu on the display (output means 12.2) using the keyboard (input means 12.3) of the user console 12, choose "Head" from the patient menu and select a mode of operation, i.e., a series of parameters under which respective ones of the units associated with the brain coil of the magnet/coil device 4 are to operate to scan the brain of the patient. These parameters are known per se in the art and thus, will not be described in detail. Furthermore, in this example, the brain coil constitutes what may be referred to as a 3D localizer of the MRI system 1.

Also, the protocol selected by the MRI technician may effect a localizer scan by the MRI system 1. A localizer scan is one that determines the planes in the brain along which the imaging is carried out and conducts a scan along those planes to produce images of the anatomical region of interest. These images may be displayed by the MRI system 1 on the display (output means 12.2) for observation by the MRI technician. One or more of these localizer images is selected by the MRI technician as the anatomical planning image used to plan for the next step which is a spectroscopy process. For example, an image that reveals a tumor, by virtue of a region in the images of a particular contrast, is selected as the anatomical planning image and the anatomical planning image is stored in a memory of the control unit 7. Although several actual images each of the tumor may be selected as the anatomical planning image used in the spectroscopy process S200, for simplicity, the process as applied to the use of only one image will be described.

The spectroscopy process S200 is carried out on the region of interest using the anatomical planning image. The spectroscopy process S200 comprises positioning a spectroscopic single voxel within the region of interest (S210) and acquiring spectral data from that part of the region of interest confined to the single voxel, i.e., a spectrum of emissions indicative of metabolite concentrations in that part of the region of interest confined to the single spectroscopic voxel (S220).

More specifically, in step S210, the MRI technician observes a "guide map" of areas of the anatomical planning image having different degrees of homogeneity of the magnetic field (S210A), and operates the MRI system, as guided by the map, to place the single spectroscopic voxel at an optimal location (described in more detail below) in the region of interest (S210B). The guide map is thus basically an overlay of a magnetic field inhomogeneity map and the anatomical planning image (refer to FIG. 4 and the description thereof below), and may be automatically generated by the MRI system 1 and output on the display (output means 12.2 of) the user console 12 of the MRI system 1.

Magnetic field maps in which variations in a characteristic, namely, the frequency, of the magnetic field $B_0$ produced by an MRI system for use in an MRI scan are known in the art, per se. The reason why the magnetic field $B_0$ can vary across the ROI is that the magnetic field $B_0$ is distorted by differences in the composition of tissue making up the ROI. For example, in the case of a tumor, the tumor may have an apoptosis or may be hemorrhaging in which case the iron in the blood will distort the magnetic field $B_0$. However, such magnetic field maps have heretofore only been produced in connection with chemical shift imaging (multi-voxel spectroscopy) for use in evaluating the quality or correctness of the process used to obtain the 2D and 3D spectroscopic data.

Figure 3:
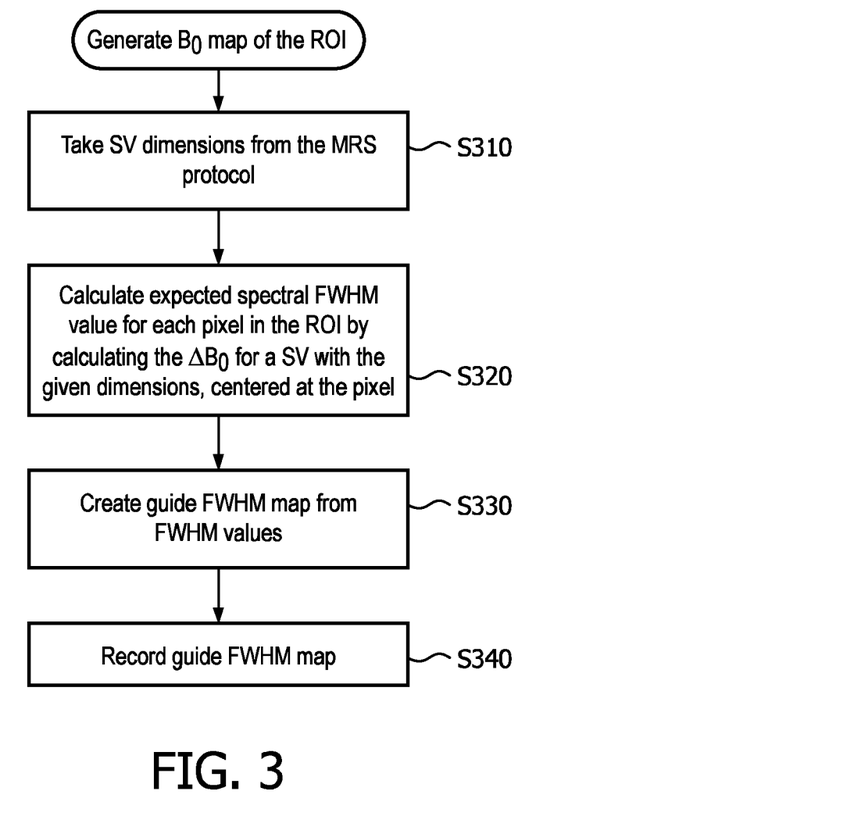
FIG. 3 is a flowchart of a sub-routine for obtaining variations in a magnetic field used to conduct an MRI scan, according to a representative embodiment.

FIG. 3 illustrates a subroutine that may be performed by an MRI system for creating a magnetic field inhomogeneity map, reflecting $\Delta B_0$, for use in step S210.

The MRI system creates a 2D or 3D imaging pixel of a certain size based on the protocol selected by the MRI technician (S310). The imaging pixel may be created according to a program or data stored in the control unit of the MRI system such as control unit 7 in the MRI system 1 of FIG. 1, for example. The imaging pixel will generally be of the same size as that of the single voxel to be used later in the acquisition of the spectral data (S220). Then, the MRI system steps a spectroscopy voxel across the ROI in accordance with an array of the imaging pixels in the ROI. In particular, the MRI system centers the spectroscopy voxel at an imaging pixel in the ROI, calculates the full-width-half-maximum (FWHM) of a frequency characteristic of the magnetic field $B_0$ at the imaging pixel and assigns the measured FWHM characteristic to the imaging pixel that is central to the spectroscopy voxel. The algorithm then moves the spectroscopy voxel to the next imaging pixel in the array and repeats the calculation. This is then repeated until all the imaging pixels have an FWHM value assigned to them. This process (S320) creates a guide-FWHM map of FWHM contour lines (S330). The contour lines are those along which chemical shifts within predetermined ranges of FWHM are observed as a result of a scan of the ROI with a magnetic field $B_0$ of a given strength, e.g., 1.5 T, 3 T or 7 T. That is, the number of contour lines and the ranges of chemical shifts to be represented by the contour lines are predetermined based on the field strength and the selected ROI. They may be set by the MRI technician or may by the MRI system manufacturer as part of the configuration of the MRI system.

Data representing the contour lines of the guide-FWHM map may then be recorded, e.g., stored in a memory of the control unit 7 of the MRI system 1 (S340).

Figure 4:
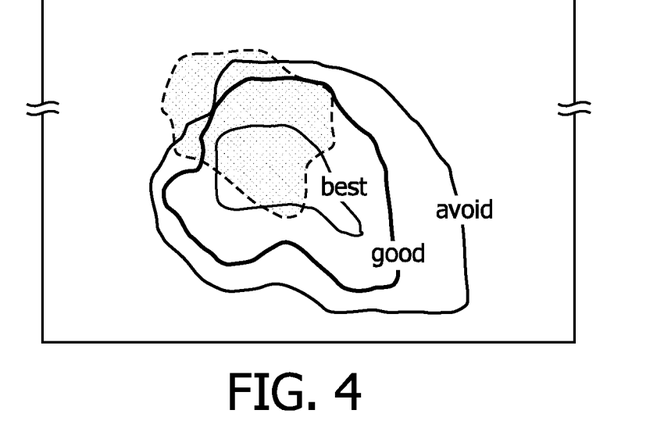
FIG. 4 is a diagram of a guide map produced, according to a representative embodiment, for use in the positioning of a single voxel in a region of interest in an MRS process.

FIG. 4 illustrates an example of a guide map produced from the anatomical planning image and the data of $\Delta B_0$ (i.e., the guide-FWHM map).

In FIG. 4, the shaded area represents a tumor. That is the dashed lines show the demarcation of the tumor from other brain tissue in the region of interest. In the example shown in FIG. 4, in which a region of the brain constitutes the ROI, 3 contour lines—"best", "good", and "avoid"—are displayed and the ranges of chemical shifts along the contour lines are: {"best"=$0<\Delta B_0<0.03$ ppm; "good"=$0.03$ ppm$<\Delta B_0<0.1$ ppm; and "avoid"=$\Delta B_0>0.1$ ppm}. In terms of Hertz, a working example may be {"best"=$0<\Delta B_0<5$ Hz; "good"=$5$ Hz$<\Delta B_0<15$ hz; and "avoid"=$\Delta B_0>30$ Hz}

Therefore, it can be appreciated that the area bounded by the contour lines are areas of the anatomical planning image in which the degrees of homogeneity of the magnetic field are different from one another. In addition, the contour lines and hence, the areas bounded by the contour lines can be color-coded to allow the MRI technician to discriminate the best area of magnetic field homogeneity from the merely good area(s) and area(s) to be avoided. Although not shown, the "best" contour line may be displayed as a green contour line, the "good" contour line may be displayed as a yellow contour line and the "avoid" contour line may be displayed as a red contour line.

Now, and by observing the guide map such as that shown in FIG. 4, the MRI technician can execute the placement of the single voxel by the MRI system 1 not only within the ROI as dictated by the anatomical planning image, i.e., at some place within the bounds of the tumor, but also at a location where the best results for the MRS can be expected. In this example, the guide map will guide the MRI technician to place the single voxel within the bounds of the tumor and at a location where the magnetic field has the greatest degree of homogeneity (within the region bounded by the "best" contour line, i.e., the region where the smallest value(s) of FWHM are calculated). Therefore, when the magnetic field used to acquire the spectral data (S220) is shimmed in the MRS process, the single voxel will be positioned precisely within the bounds of the tumor at a location where the best results of the shimming can be expected.

Figure 5A:
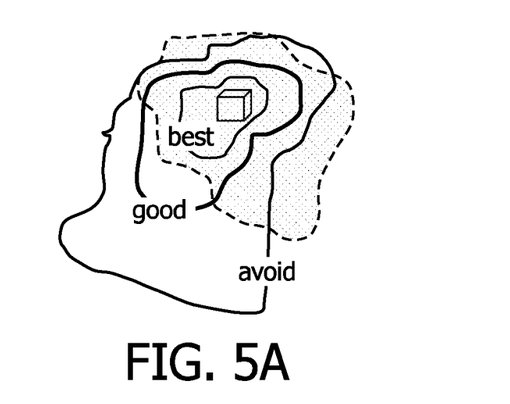
FIG. 5A is a conceptual diagram illustrating an example of the production of a guide map and the placement of a single voxel using the guide map in the case of a relatively small single voxel.
Figure 5B:
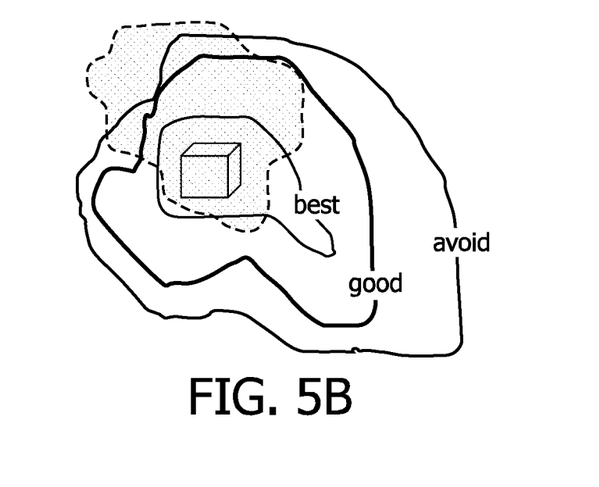
FIG. 5B is a conceptual diagram illustrating an example of the production of a guide map and the placement of a single voxel using the guide map in the case of a relatively large single voxel.

Note, it will be readily appreciated that the layouts of the contour lines are a function of the size of the imaging voxel. This is shown in FIGS. 5A and 5B. Specifically, FIG. 5A shows the case in which the protocol resulted in the creation of the magnetic field map using a relatively small imaging voxel, and the location where the correspondingly small single voxel for MRS is placed under the guidance of that map. FIG. 5B shows the case in which the protocol resulted in the creation of the magnetic field map using a relatively large imaging voxel, and the location where the correspondingly large single voxel for MRS is placed under the guidance of that map.

According to another representative embodiment, the MRI system 1 may also automatically determine an optimal size for the imaging voxel and corresponding single voxel to be used in the acquisition of the spectral data (S220). The MRI system 1 may make such a determination based on several factors such as the size of any region of overlap between the tumor and the area on the guide map where the homogeneity of the magnetic field is the greatest.

The MRI system 1 may also factor in the dependence of SNR levels on voxel size to determine the optimal size for the single voxel. For example, the MRI system 1 may ensure that the single voxel is not too small as to produce output having an insufficient signal-to-noise ratio (SNR).

Furthermore, the software of the MRI system 1 may then give the MRI technician the option to overlay a magnetic field map, produced using an imaging voxel of the optimized size, on the anatomical image, for use in planning the single voxel (S210B). In this case, the planning of the single voxel might not only entail locating the single voxel within the region of interest but resizing the voxel so as to deviate from that originally indicated by the protocol. Accordingly, the MRI system may determine and display (on output means 12.2) the suggested optimally sized imaging voxel and suggested location for the corresponding spectroscopic single voxel that will produce the best results, in conjunction with the shimming of the magnetic field within user-specified full-width half max (FWHM) shimming requirements.

Once the spectroscopic single voxel is located within the ROI under the guidance provided by the guide map (automatically or by the technician through observation of the guide map), the spectral data from the tissue confined to the single voxel is acquired by the spectrometer of the MRI system through processes such as setting the parameters of the transmitter which transmits the magnetic field to the single voxel, shimming the magnetic field, suppressing the water signal, etc. These processes may be conventional, per se, and thus will not be described in detail.

Figure 6A:
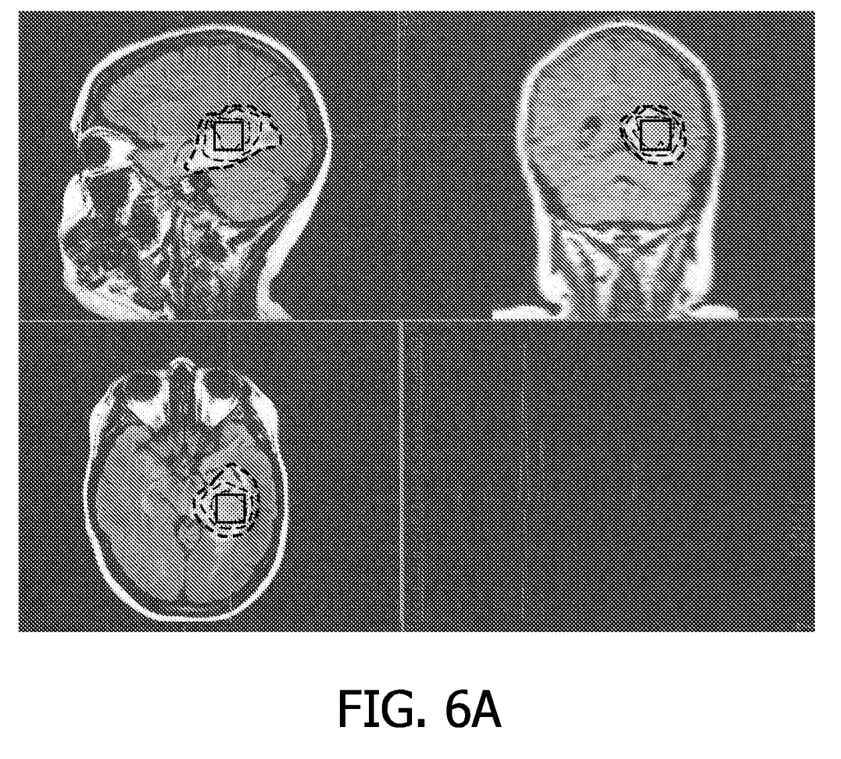
FIG. 6A is an example of an anatomical planning image, a guide map including a single voxel overlayed on the anatomical planning image, and a graph spectral data acquired from the region confined to the single voxel using a method according to a representative embodiment.
Figure 6B:
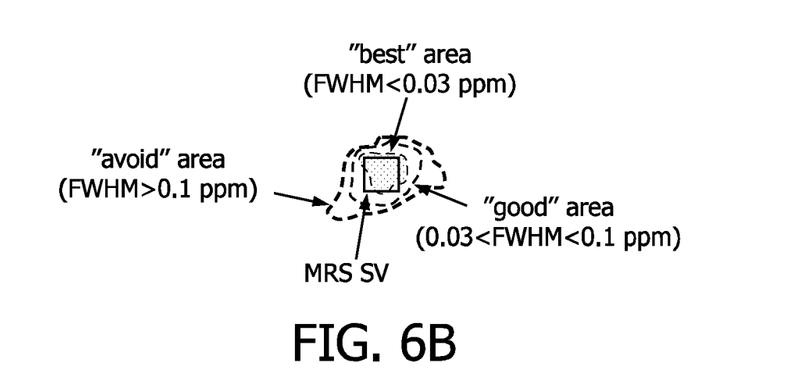
FIG. 6B is a diagram of the guide map showing examples of the values of FWHM used to form the contour lines of the guide map.

FIGS. 6A and 6B show an example of the anatomical planning image, the spectroscopy SV, and spectral data that can produced by a spectrometer as part of the MRI system, all in accordance with aspects of representative embodiments as described above.

Although the case has been described in which an MRI technician operates the MRI system based on his or her observation of the guide map to place the single voxel in an optimal location, it will be appreciated that the process may instead be fully automated in cases where there is a demarcation (such as tumor segmentation). To this end, the MRI system 1 may process the anatomical planning image to derive image processing data representing a demarcated region of the anatomical planning image (in this example, as provided by the tumor). The image processing data and the magnetic field data $\Delta B_0$ (data representing the guide-FWHM map in this example), are then processed to determine the size and location of an area of overlap between the tumor and the area where the homogeneity of the magnetic field is the greatest. The MRI system than places the single voxel in the area of overlap and acquires the spectral data from the region confined to the single voxel. This will be described in more detail as follows.

A non-transitory computer readable medium, such as one embodied by a software package, may be provided for automated planning of the spectroscopic single voxel. Preferably, the package includes operating instructions, which are often referred to herein as "code segments," for controlling the MRS imaging system for a fully automated run of the single voxel spectroscopy process. To this end, the package can be enhanced with optional operational instructions to be selected by the technician, as well as interaction points where the technician can modify, accept, or reject the results of the automated positioning of the spectroscopic single voxel.

More specifically, preferably, the package as run will order a well-structured list of scans and processing steps that compose a multi-sequence examination, and order the imaging system to display icons indicating scan status, actions needed, and upcoming acquisitions. The computer readable non-transitory medium may also include, as an integral or separate part of the software package, a complete list of ready-to-use scan protocols which, like the automatic scan planning component, run completely autonomously at the touch of a button such that various types of processing according to end user preferences is performed without supervision. The computer readable non-transitory medium may comprise one or more functional blocks or units of the processor of the imaging system, e.g., memory and control units. That is, the computer readable non-transitory medium may comprise software loaded into the imaging system, the processor of the imaging system configured with software or firmware, or combinations thereof that enable the imaging system to perform a multi-sequence examination which includes two or more pre-scans followed by the spectroscopic single voxel scan. The pre-scans may run fully automatically without the need of any user interface.

The first pre-scan, for example, acquires the anatomical planning image that is then processed by an automated segmentation tool, either directly in the scanner, or on a separate disk/console dedicated to this end. This pre-scan can also be acquired separately and then used automatically by the computer readable non-transitory medium. The segmentation tool automatically segments the tumor at its margins. This segmentation can be a 2D (in-plane) or a 3D segmentation. In the case in which this delineation is fully automatic, the technician is also presented with the option of configuring the processor such that he/she can inspect and modify the final segmentation results. These results are then sent to a console of the imaging system.

The second pre-scan acquires the $B_0$ and/or susceptibility data that is then used to automatically generate the FWHM values of the guide-FWHM map. After the initial two pre-scans, the technician may be presented with the guide map in the form of the anatomical planning image with an overlay of the segmentation margins and the guide-FWHM map. The package is configurable such that the display of both the segmentation margins and the guide map are optional. In its fully automated mode, the imaging system will not display either of these to the technician.

Next, the technician can use the three scans (i.e., the "3-point planscan" put in place by this example of the computer readable non-transitory medium) to deposit an initial choice for the center of the spectroscopic single voxel. The computer readable non-transitory medium can then automatically optimize the voxel position, orientation, and size of the voxel, and will present the technician with the options to accept, modify, or cancel the proposed voxel planning. The computer readable non-transitory medium may also include a memory in which a user-specific database of the technician's choices are stored, and may be configured to modify the algorithms which constitute the instructions which effect the 3-point plan scan. That is, the computer readable non-transitory medium may be configured to take into account any modifications that the technician performed in executing any future voxel plannings, i.e., the computer readable non-transitory medium may be "self-taught".

According to representative embodiments as described above, a guide map of areas of an anatomical planning image of different degrees of homogeneity of the magnetic field is produced. The guide map is produced based on a magnetic field map indicative of the homogeneity/inhomogeneity of the magnetic field over a region of interest as correlated with a spectroscopic single voxel of a particular size. The guide map is used to place a spectroscopic single voxel of that size at a location within the region of interest.

Also, embodiments are described in which overlay data of areas of an anatomical planning image of different degrees of homogeneity of the magnetic field is produced, and used in automatically sizing or sizing and positioning of a spectroscopic single voxel within the region of interest.

In the case of a tumor, for example, the guide map/overlay data accounts for inhomogeneity in the tumor itself and in the environment surrounding the tumor such that placement of the single voxel is not carried out merely on the demarcation of the tumor as observed through the anatomical planning image as may currently be the case. Thus, the guide map/overlay data can be used to place the spectroscopic single voxel at an optimal location for the spectroscopy.

Finally, embodiments of the inventive concept and examples thereof have been described above in detail. The inventive concept may, however, be embodied in many different forms and should not be construed as being limited to the embodiments described above. Rather, these embodiments were described so that this disclosure is thorough and complete, and fully conveys the inventive concept to those skilled in the art. Thus, the true spirit and scope of the inventive concept is not limited by the embodiment and examples described above but by the following claims.

What is claimed is:

1. A method for conducting single voxel of magnetic resonance spectroscopy (MRS) in a magnetic resonance imaging (MRI) system, the method comprising:

exposing a region of interest to a magnetic field using the MRI system;

producing an anatomical MRI planning image of the region of interest including an anatomical structure of interest;

analyzing the magnetic field for its homogeneity over the region of interest;

based on the analysis of the magnetic field, producing a magnetic field homogeneity map depicting areas of the anatomical planning image of different degrees of homogeneity of the magnetic field;

calculating a size of a spectroscopic single voxel based on a size of a region of overlap between an area of greatest magnetic field homogeneity and the anatomical structure of interest;

positioning the spectroscopic single voxel of the calculated size within the region of overlap of the anatomical region of interest and the area of greatest homogeneity; and acquiring a magnetic resonance spectrum from the spectroscopic single voxel.

2. The method of claim 1, wherein the anatomical structure of interest is a tumor.

3. The method of claim 1, wherein the anatomical planning image and the magnetic resonance spectrum are obtained sequentially.

4. The method of claim 1, wherein the analyzing comprises stepping a spectroscopic voxel across the region of interest, measuring a characteristic of the magnetic field at the spectroscopic voxel each time the spectroscopic voxel is located at a new position as the result of the stepping, and calculating FWHM in a characteristic of the magnetic field at each position of the spectroscopic voxel.

5. The method of claim 1, wherein the producing of the map comprises demarcating at least three areas of the anatomical planning image in which the degrees of homogeneity of the magnetic field are different from one another.

6. The method of claim 5, wherein the producing of the map comprises displaying contours of the at least three areas.

7. The method of claim 5, wherein the producing of the map comprises color coding the at least three areas.

8. The method of claim 1, further including:
demarcating the anatomic structure in the anatomical planning image;
denoting the region of greatest magnetic field homogeneity on the map; and
superimposing the anatomical planning image and the magnetic field homogeneity map.

9. A magnetic resonance imaging system comprising:
a magnet/coil system configured to generate a magnetic field in a region of interest and to induce magnetic resonance in the region of interest; and
a control system configured to control the magnet and coil system to perform the method of claim 1.

10. The system of claim 9, further comprising a console including a display, and wherein the control system is configured to control the display to display the magnetic field homogeneity map during a single voxel spectroscopy mode.

11. The system of claim 10, wherein the magnetic field homogeneity map comprises at least three areas of the anatomical planning image in which degrees of homogeneity of the magnetic field are different from one another.

12. The system of claim 11, wherein the magnetic field homogeneity map comprises contour lines at boundaries between adjacent ones of the at least three areas.

13. The system of claim 11, wherein the at least three areas are color coded to differentiate themselves from one another.

14. The system of claim 9, wherein the control system is configured to demarcate the anatomical structure of interest in the anatomical planning image, calculate the size of the spectroscopic single voxel, and locate the spectroscopic single voxel within the region of interest based on the overlay automatically while the system is in a single voxel spectroscopy mode.

15. A method of conducting single voxel magnetic resonance spectroscopy (MRS), the method comprising:
obtaining an anatomical planning image of a region of interest including an anatomical structure of interest;
acquiring a magnetic field map, the magnetic field map denoting areas of the region of interest having different degrees of homogeneity of the magnetic field;
superimposing the anatomical planning image and the magnetic field homogeneity map;
calculating a size of a spectroscopic single voxel based on a size of an area of overlap between an area of greatest magnetic field homogeneity and the anatomical structure of interest;
positioning the spectroscopic single voxel of the calculated size within the overlap of the anatomical structure of interest and the area of greatest magnetic field homogeneity of the magnetic field map; and
acquiring a spectrum of magnetic resonances from the spectroscope single voxel.

16. The method of claim 15, wherein the anatomical planning image is obtained as a separate scan from a scan that produces the spectrum of magnetic resonances.

17. A non-transitory computer-readable medium carrying software for controlling one or more computer processors to perform the method of claim 15.

18. An apparatus for conducting single voxel magnetic resonance spectroscopy (MRS), the apparatus comprising:
one or more processors configured to:
receive magnetic resonance imaging data and magnetic field homogeneity data from a region of interest of a magnetic resonance system,
reconstruct the magnetic resonance imaging data into an anatomical planning image of the region of interest, the anatomical planning image including an anatomical structure of interest,
generate a magnetic field map denoting areas of the region of interest having each of a plurality of degrees of magnetic field homogeneity,
superimpose the anatomical planning image and the magnetic field homogeneity map,
determine an area of overlap of the anatomical structure of interest and an area of greatest magnetic field homogeneity in the superimposed planning image and the magnetic field homogeneity map,
calculating a size for a spectroscopic single voxel based on the area of overlap between the anatomical structure of interest and the area of greatest magnetic field homogeneity,
positioning the spectroscopic single voxel of the calculated size within the overlap of the anatomical region of interest and the area of greatest magnetic field homogeneity, and
controlling the magnetic resonance system to acquire a magnetic resonance spectrum confined to the spectroscopic single voxel.

19. The apparatus of claim 18, wherein the magnetic resonance system includes:
a magnet and coil system configured to generate a magnetic field in the region of interest and to induce and receive magnetic resonance imaging data and the magnetic resonance spectrum from the region of interest.

20. The apparatus of claim 19, further including:
a display device configured to display at least one of:
the superimposed anatomical planning image and magnetic field homogeneity map, and
the acquired magnetic resonance spectrum.

21. The apparatus of claim 19, further including:
a display device configured to display the superimposed anatomical planning image and the magnetic field homogeneity map.

22. The apparatus of claim 21, wherein the anatomical structure of interest is demarcated in the anatomical planning image and the areas of different magnetic field homogeneity are color coded in the magnetic field homogeneity map.

23. The apparatus of claim 21, wherein the anatomical structure of interest is demarcated in the anatomical planning image and the areas of different magnetic field homogeneity are denoted by contours.

* * * * *